(12) United States Patent
Xiong et al.

(10) Patent No.: US 11,147,778 B2
(45) Date of Patent: Oct. 19, 2021

(54) SIDEROPHORE-POLYMER CONJUGATES FOR INCREASING BACTERIAL SENSITIVITY TO ANTIBIOTICS

(71) Applicant: Wisconsin Alumni Research Foundation, Madison, WI (US)

(72) Inventors: May Xiong, Middleton, WI (US); Max Purro, Athens, GA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 238 days.

(21) Appl. No.: 16/407,456

(22) Filed: May 9, 2019

(65) Prior Publication Data

US 2019/0269631 A1 Sep. 5, 2019

Related U.S. Application Data

(63) Continuation of application No. 15/685,954, filed on Aug. 24, 2017, now Pat. No. 10,328,038.

(60) Provisional application No. 62/379,121, filed on Aug. 24, 2016, provisional application No. 62/532,879, filed on Jul. 14, 2017.

(51) Int. Cl.

| | |
|---|---|
| *A61K 9/127* | (2006.01) |
| *A61K 31/164* | (2006.01) |
| *A61K 31/7048* | (2006.01) |
| *A61K 47/60* | (2017.01) |
| *A61K 47/69* | (2017.01) |
| *C07F 13/00* | (2006.01) |
| *C08G 65/06* | (2006.01) |
| *A61K 31/16* | (2006.01) |
| *A61K 33/06* | (2006.01) |
| *A61K 33/24* | (2019.01) |
| *A61K 33/26* | (2006.01) |
| *A61K 33/30* | (2006.01) |
| *C12N 1/20* | (2006.01) |

(52) U.S. Cl.
CPC ............ *A61K 31/164* (2013.01); *A61K 31/16* (2013.01); *A61K 31/7048* (2013.01); *A61K 33/06* (2013.01); *A61K 33/24* (2013.01); *A61K 33/26* (2013.01); *A61K 33/30* (2013.01); *A61K 47/60* (2017.08); *A61K 47/6907* (2017.08); *C07F 13/00* (2013.01); *C08G 65/06* (2013.01); *C08G 2650/58* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 2005/0123602 A1 | 6/2005 | Michaelis | |
| 2007/0231406 A1 | 10/2007 | Bucalo et al. | |
| 2008/0085866 A1 | 4/2008 | Greenberg et al. | |
| 2012/0220651 A1* | 8/2012 | Chevion | ................. A61P 11/00 514/494 |
| 2019/0125670 A1* | 5/2019 | Giri | .................... A61K 41/0057 |

OTHER PUBLICATIONS

Araki, et al., "Efficient production of polyrotaxanes from a-cyclodextrin and poly (ethylene glycol)," Macromolecules, Jul. 16, 2005, vol. 38, No. 17, pp. 7524-7527.
Coyle, "Manual of antimicrobial susceptibility testing," American Society for Microbiology, 2005.
Ford, et al., "Colorimetric determination of erythromycin," Analytical Chemistry, Aug. 1953, vol. 25, No. 8, pp. 1195-1197.
Hentzer, et al., "Alginate overproduction affects Pseudomonas aeruginosa biofilm structure and function," Journal of Bacteriology, Sep. 2001. vol. 183, No. 18, pp. 5395-5401.
International Search Report and Written Opinion in International Application No. PCT/US2017/048483, dated Nov. 13, 2017 (17 pages).
Moreau-Marquis, et al., "Tobramycin and FDA-Approved Iron Chelators Eliminate Pseudomonas aeruginosa Biofilms on Cystic Fibrosis Cells," American Journal of Respiratory Cell and Molecular Biology, 2009, vol. 41, pp. 305-313.
Obrien, et al., "Investigation of the Alamar Blue (resazurin) fluorescent dye for the assessment of mammalian cell cytotoxicity," European Journal of Biochemistry, Jun. 2000, 267, No. 17, pp. 5421-5426.
OToole, et al., "Flagellar and twitching motility are necessary for Pseudomonas aeruginosa biofilm development," Molecular Microbiology, Oct. 1998, 30, No. 2, pp. 295-304.
Rossi, et al., "In Vitro Chelating, Cytotoxicity, and Blood Compatibility of Degradable Poly(Ethylene Glycol)—Based Macromolecular Iron Chelators," Biomaterials, 2009, 30, pp. 638-648.
Savage, et al., "Antibacterial properties of cationic steroid antibiotics," FEMS Microbiology Letters, Oct. 22, 2002, 217, No. 1, pp. 1-7.
Wilks, et al., "Imaging PEG-Like Nanoprobes in Tumor, Transient Ischemia, and Inflammatory Disease Models," Bioconjugate Chemistry, 2015, pp. 1061-1069.

* cited by examiner

*Primary Examiner* — Susan T Tran

(74) *Attorney, Agent, or Firm* — Foley & Lardner LLP

(57) ABSTRACT

The present technology provides siderophore-polymer conjugates that enhance the sensitivity of bacteria to antibiotics, e.g., *Pseudomonas, P. aeruginosa, Acinetobacter*, and *A. baumannii*. Methods of preparing and using such conjugates to treat bacterial infections are disclosed.

19 Claims, 13 Drawing Sheets

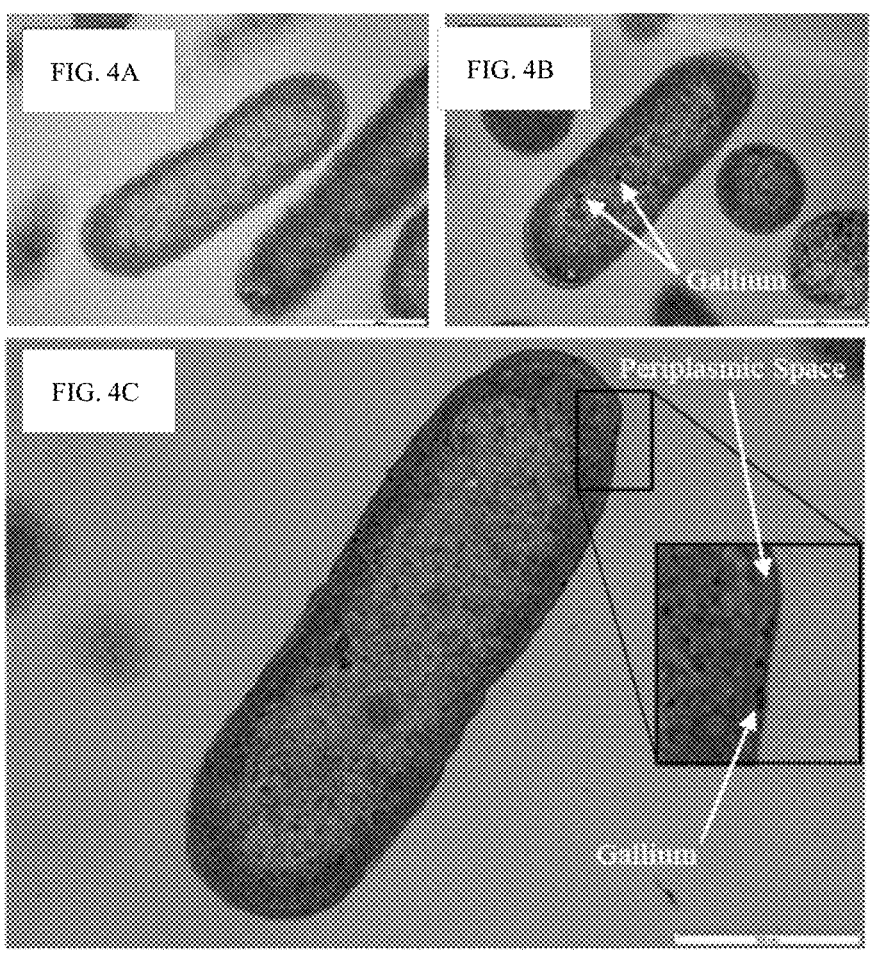

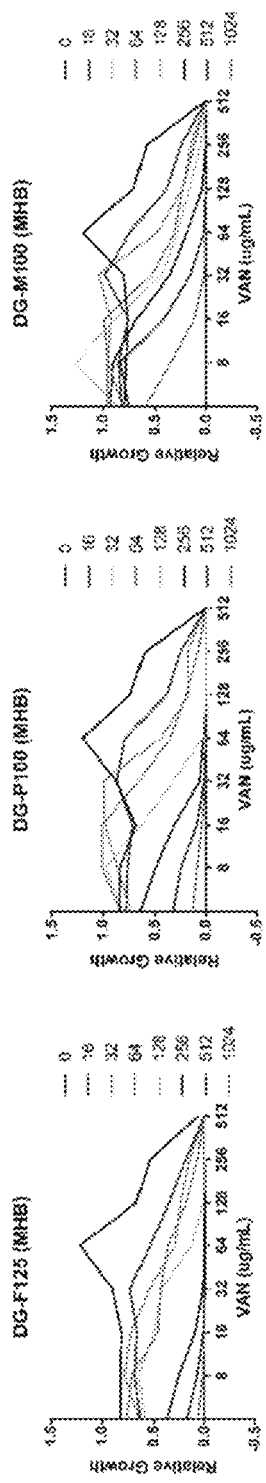
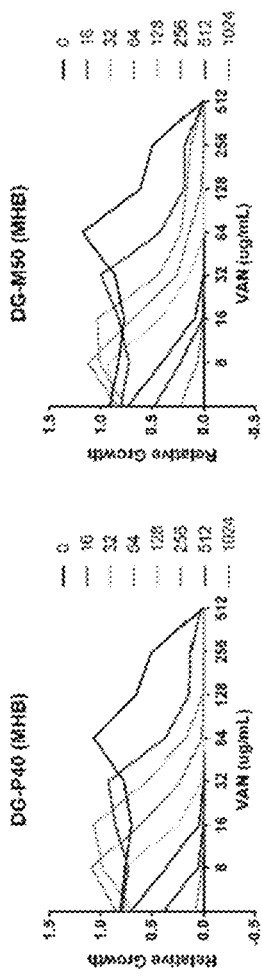
FIG. 8A
FIG. 8B
FIG. 8C
FIG. 8D
FIG. 8E

SIDEROPHORE-POLYMER CONJUGATES FOR INCREASING BACTERIAL SENSITIVITY TO ANTIBIOTICS

CROSS-REFERENCE TO RELATED APPLICATIONS

This application is a divisional of U.S. patent application Ser. No. 15/685,954, filed Aug. 24, 2017, which claims priority to and benefit of U.S. Provisional Application No. 62/379,121, filed on Aug. 24, 2016, and to U.S. Provisional Application No. 62/532,879, filed on Jul. 14, 2017. The contents of each are incorporated herein in their entireties.

GOVERNMENT RIGHTS

This invention was made with government support under DK099596 awarded by the National Institutes of Health. The government has certain rights in the invention.

FIELD

The present disclosure relates generally to siderophore-polymer conjugates and methods of preparing and using such conjugates to increase bacterial sensitivity to antibiotics. In particular, the present conjugates of poloxamers and PEG increase sensitivity of *Pseudomonas* bacteria such as *P. aeruginosa* and other bacteria to antibiotics.

BACKGROUND

The increasing prevalence of antibiotic resistance, combined with the diminished pace of antibiotic discovery, represents a major public health threat. In general, the common modes of resistance fall under several categories: restricted uptake, increased efflux, drug inactivation, and target alteration. In some species of bacteria such as *Pseudomonas aeruginosa* for example, the particularly impermeable outer membrane provides a broad spectrum of intrinsic resistance, especially against large and/or hydrophobic antibiotics. Yet little research has been done on strategies to combat this specific mechanism of resistance.

SUMMARY

The present technology provides siderophore-polymer conjugates that complex with a metal and increase bacterial sensitivity to antibiotics, e.g., *Pseudomonas*, and especially *P. aeruginosa*. The polymer may be a poloxamer or a poly(ethylene glycol) ("PEG"), and the siderophore may be desferrioxamine B (DFO). A variety of metal ions such as Fe(III) and Ga(III), among others, may complex with the siderophore. The conjugate metal complex and an antibiotic may be administered to a subject suffering from a bacterial infection to treat the infection. Use of the polymer-conjugated metal complex may improve the effectiveness of the antibiotic, even in certain drug-resistant strains of *P. aeruginosa*.

BRIEF DESCRIPTION OF THE DRAWINGS

FIGS. 4A-4C are tunneling electron micrographs of *P. aeruginosa* not exposed to any drug as control (4A), *P. aeruginosa* exposed to DFO(Ga) with uptake into cytoplasm (4B), and *P. aeruginosa* exposed to F127-(DFO-Ga)$_2$, where conjugate is localized to periplasmic space (4C).

FIGS. 8A-8E shows ATCC 27853 dose response between VAN and varying the concentration of DG-F125, DG-P100, DG-M100, DG-P40, or DG-M50.

FIGS. 11A and 11B respectively show CLSM image of ATCC 27853 biofilm in presence of MHB as a positive control, and the CLSM image of the ATCC 27853 biofilm in the presence of 32/ug/mL VAN+64 uM F127-(DFO-Ga)$_2$.

FIGS. 11C and 11D respectively show CLSM image of PAO1 biofilm in presence of MHB as a positive control, and the CLSM image of the PAO1 biofilm in the presence of 64/ug/mL VAN+64 uM F127-(DFO-Ga)$_2$.

DETAILED DESCRIPTION

Figure 1:
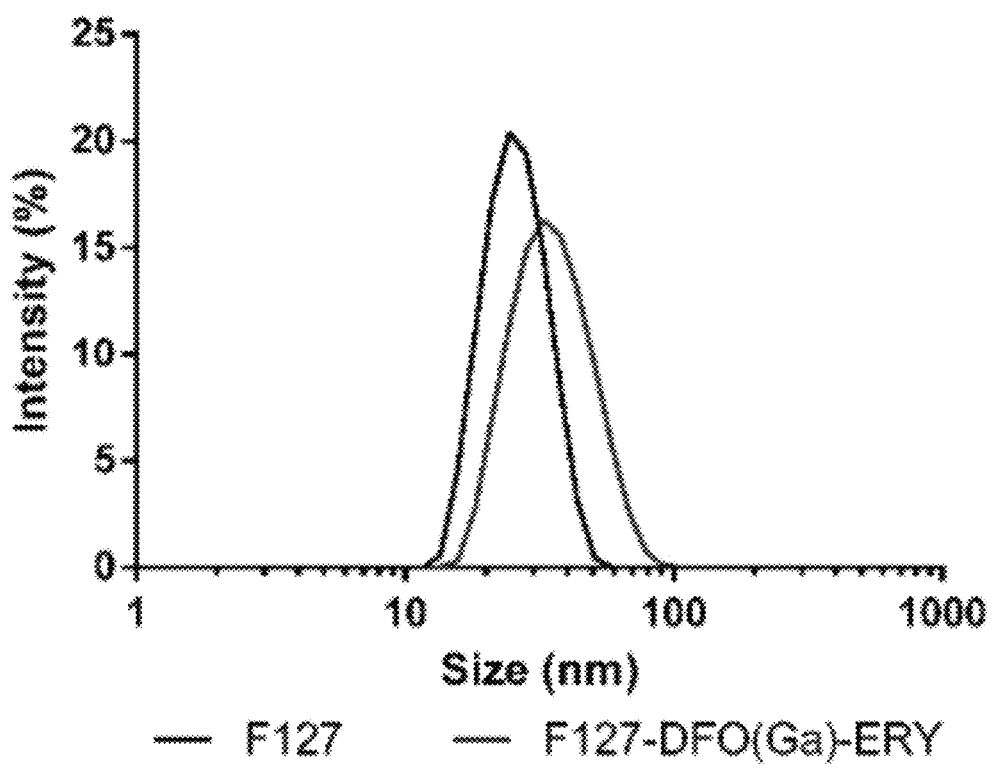
FIG. 1 shows an illustrative embodiment of the present technology as assessed by dynamic light scattering. The results are consistent with the formation of micelles in PBS at 37° C.: F127=24.9 nm (polydispersity (PDI)=0.045) and F127-DFO(Ga)-ERY=32.9 nm (PDI=0.111).
Figure 2A:
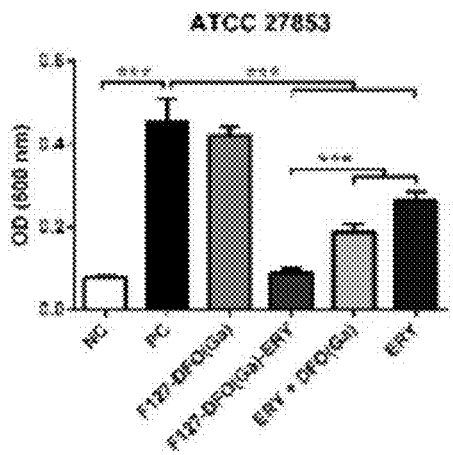
FIGS. 2A-2E shows the antibacterial activity of an illustrative embodiment, F127-(DFO-Ga)$_2$/ERY against reference and MDR strains of *P. aeruginosa*. *=(p<0.001) and =(p<0.01). Antibiotic abbreviations: DOR=doripinem; IPM=imipenem; MEM=meropenem; FEP=cefepime; CAZ=ceftazidime; TZP=piperacillin-tazobactam; CIP=ciprofloxacin; TOB=tobramycin.
Figure 2B:
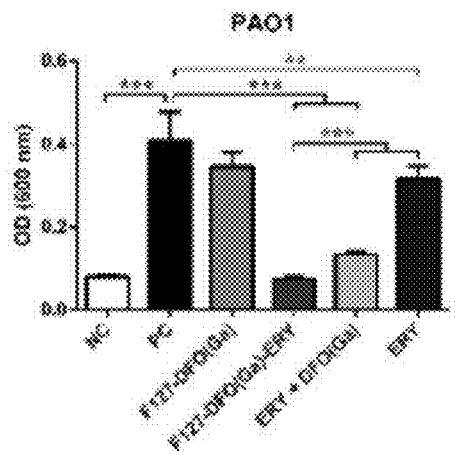
Figure 2C:
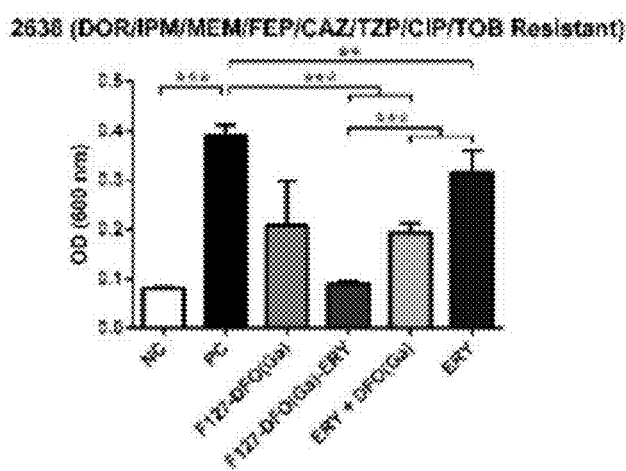
Figure 2D:
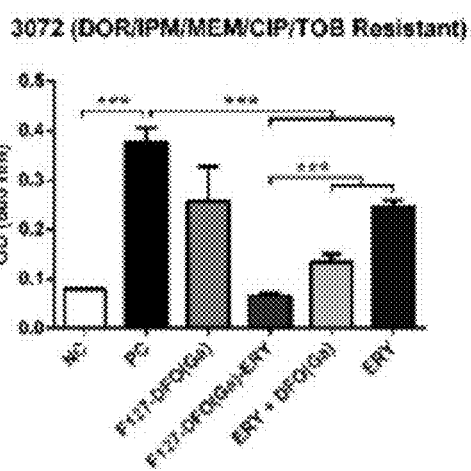
Figure 2E:
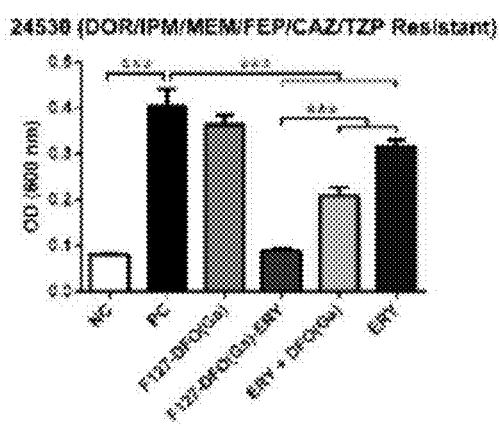

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "alkyl groups" include straight chain and branched chain alkyl groups having 1, 2, 3, 4, 5, or 6 carbon atoms. Examples of straight chain alkyl groups include groups such as methyl, ethyl, n-propyl, n-butyl, n-pentyl, and n-hexyl. Examples of branched alkyl groups include, but are not limited to, isopropyl, iso-butyl, sec-butyl, tert-butyl, neopentyl, isopentyl, and 2,2-dimethylpropyl groups. Alkyl groups are unsubstituted unless otherwise indicated.

"Desferrioxamine B" (a.k.a. "deferoxamine" or "desferoxamine B") is a bacterial siderophore having the chemical name N'-{5-[acetyl(hydroxy)amino]pentyl}-N-[5-({4-[(5-aminopentyl)(hydroxy)amino]-4-oxobutanoyl}amino)pentyl]-N-hydroxysuccinamide and the following structure.

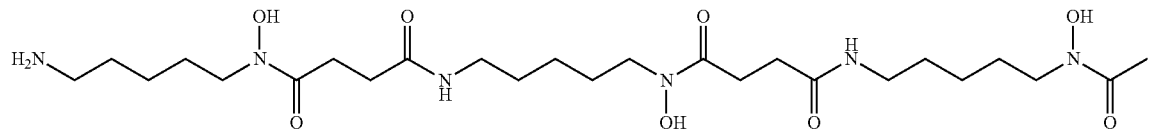 [SMILES: CC(=O)N(O)CCCCCNC(=O)CCC(=O)N(O)CCCCCNC(=O)CCC(=O)N(O)CCCCCN]

"Siderophore" as used herein refers to bacterial siderophores, i.e., molecules secreted by bacteria that tightly bind to iron (in its ionic form) and allows the bacteria to internalize the siderophore-iron complex for its own use. Siderophores of the present technology may bind other metal ions as well, e.g., Ga, Zn, Co, and Al. Thus, a "siderophore-metal complex" refers to a non-covalent binding complex between the metal ion and the siderophore.

A "hydrophobic drug" refers to a water insoluble drug. A water insoluble drug has a solubility of less than 0.1 mg/mL in distilled water at 25° C. Within the context of this disclosure, a "slightly soluble drug" has a solubility of about 1-10 mg/mL and a "very slightly soluble drug" has a solubility of about 0.1-1 mg/mL. These terms are well-known to those of skill in the art. See, e.g., Martin (ed.), *Physical Pharmacy*, Fourth Edition, page 213 (Lea and Febiger 1993).

"Molecular weight" as used herein with respect to polymers refers to weight average molecular weights ($M_w$) and can be determined by techniques well known in the art including gel permeation chromatography (GPC). GPC analysis can be performed, for example, on a Styragel HR-3 column calibrated with PEG using RI detection and chloroform as the eluent.

The present technology provides pharmaceutical compositions and medicaments comprising any of one of the embodiments of the conjugates disclosed herein, an antibiotic and a pharmaceutically acceptable carrier or one or more excipients. The compositions may be used in the methods and treatments described herein. The pharmaceutical composition may include an effective amount of any of one of the embodiments of the compositions disclosed herein. In any of the above embodiments, the effective amount may be determined in relation to a subject. "Effective amount" refers to the amount of compound or composition required to produce a desired effect. One example of an effective amount includes amounts or dosages that yield acceptable toxicity and bioavailability levels for therapeutic (pharmaceutical) use including, but not limited to, the inhibition (i.e., slowing, halting or reversing), cure or prevention of a bacterial infection in a subject. As used herein, a "subject" or "patient" is a mammal, such as a cat, dog, rodent or primate. Typically the subject is a human, and, preferably, a human at risk for or suffering from stenosis due to, e.g., a perivascular graft. The term "subject" and "patient" can be used interchangeably.

In one aspect the present technology provides a conjugate that includes a water-soluble polymer such as a poloxamer or a PEO covalently attached to at least one siderophore-metal ion complex wherein the metal is selected from Fe, Ga, Zn, Co, or Al.

"Poloxamer" as used herein refers to a nonionic triblock copolymer in which the central block of poly(propylene oxide) ("PPO") is flanked at each end by a block of poly(ethylene glycol) or PEG also known as poly(ethylene oxide) or PEO. A "water soluble poloxamer" is therefore a poloxamer as defined herein that has a solubility in water of at least 1 mg/mL at 25° C. For example, the molecular weight of PPG in the present poloxamers may be from about 800 to about 5,000 Daltons ("Da"), including e.g., about 800, about 900, about 1,000, about 1,100, about 1,200, about 1,500, about 2,000, about 2,500, about 3,000, about 3,500, about 4,000, about 4,500, about 5,000 or a range between and including any two of the foregoing values such as about 2,500 to about 4,500 Da. The percentage of PEG in micelle-forming poloxamers typically ranges from about 10% to about 80%, and in some embodiments, from about 60% to about 80%, from about 40% to about 80% or about 40% to about 70%. Examples of percentages of PEO in micelle-forming poloxamers include, e.g., about 10%, about 20%, about 30%, about 40%, about 50%, about 60%, about 70%, about 80% or a range between and including any two of the foregoing values. In some embodiments, the poloxamer has a molecular weight of about 7,000 Da to about 15,000 Da, e.g., about 7,000, about 8,000, about 9,000, about 10,000, about 11,000, about 12,000, about 13,000, about 14,000, or about 15,000 Da or a range between and including any two of the foregoing values.

In some embodiments, the water-soluble poloxamer is also a "micelle-forming poloxamer," i.e., a poloxamer capable of forming micelles; that is, each block of the poloxamer has a molecular weight that permits micelle formation in aqueous solution at concentrations above the critical micelle concentration but below the gelling concentration. However, the present technology does not require the water-soluble poloxamer to form a micelle.

Poloxamers may be prepared according to known methods, and are also commercially available from sources such as BASF (PLURONIC, KOLLIPHOR) and CRODA (SYNPERONIC). Suitable poloxamers include but are not limited to PLURONIC F127 (each block of PEO having on average 101 repeating ethylene oxide units and a block of PPO having an average of 56 repeating units; a.k.a. P407) and PLURONIC P188 (each block of PEO having on average 80 repeating ethylene oxide units and a block of PPO having an average of 27 repeating units; a.k.a. P407).

A water-soluble PEG may also be used as the water-soluble polymer in the present conjugates. In some embodiments the molecular weight of the water-soluble PEG ranges from about 200 to 20,000 Da. For example the PEG may be about 200 Da, about 500 Da, about 1,000 Da, about 2,000 Da, about 3,000 Da, about 4,000 Da, about 5,000 Da, about 7,500 Da, about 10,000 Da, about 12,500 Da, about 15,000 Da, about 17,500 Da, about 20,000 Da, or a range between and including any two of the foregoing values. In some embodiments the water soluble polymer is a PEG with a molecular weight from about 1,000 Da to about 12,500 Da The present conjugates include complexes having a siderophore. Siderophores are selected on the basis of whether the siderophore will undergo uptake by the bacteria that are to be treated. Thus for *P. aeruginosa* example, the siderophore may be desferrioxamine B (DFO), pyoverdine, or pyochelin. In some embodiments, the siderophore is covalently attached to the poloxamer or PEO through an amide bond. The siderophore forms a complex with metal ions such as Fe(III), Ga(III), Zn(II), Co(III), and Al(III). In some embodiments, the metal ion is Ga(III). In some embodiments, in an aqueous solution at a pH of 7, the metal has a log $K_a$ of at least 10 to the siderophore. In other embodiments the metal has a log $K_a$ of at least 11, at least 12, at least 13, at least 14, at least 15, at least 16, at least 17, at least 18, at least 19, at least 20, at least 25 or even at least 30.

While not wishing to be bound by theory, it is believed that the present conjugates work as follows. Once the siderophore is actively transported across the outer membrane, the polymer appears to prevent the transport channel from closing and creating an open pore through which erythromycin and other antibiotics can cross the outer membrane.

In another aspect, the present technology provides compositions including any of the conjugates described herein and an antibiotic. In some embodiments, the antibiotic may be an compound with a molecular weight greater than about 600 Da. For example, the antibiotic may be one or more selected from the group consisting of macrolides, ketolides, streptogramin, ansamycin, aminocoumarin, and glycopeptide. Nonlimiting examples include those listed in Table A. In some embodiments, the antibiotic may be a compound with a molecular weight less than about 600 Da. For example, the antibiotic may be one or more selected from the group consisting of aminoglycosides, carbapenems, cephalosporins, monobactams, penicillins, fluoroquinolones, and rifampicin. Suitable antibiotics for use with the present conjugates include one or more selected from the group consisting of erythromycin, gentamycin, tobramycin, doripenem, imipenem, meropenem, cefoperazone, ceftazidime, cefepime, ceftobiprole, aztreonam, carenicillin, piperacillin/tazobactam, colistin, ciprofloxacin, levofloxacin, rifampicin, and vancomycin. In some embodiments, the antibiotic is one or more selected from the group consisting of erythromycin, vancomycin, rifampicin, and novobiocin. The present compositions may include for example, about 0.05 wt % to about 10 wt % of the antibiotic, including but not limited to about 0.05 wt %, about 0.1 wt %, about 0.2 wt %, about 0.3 wt %, about 0.4 wt %, about 0.5 wt %, about 0.75 wt %, about 1 wt %, about 1.5 wt %, about 2 wt %, about 2.5 wt %, about 3 wt %, about 4 wt %, about 5 wt %, about 6 wt %, about 7 wt %, about 8 wt %, about 9 wt %, about 10 wt %, or a range between and including any two of the foregoing values.

TABLE A

| | Antibiotic | Class | Target | MW (g/mol)* | Computed LogP* |
|---|---|---|---|---|---|
| 1 | Erythromycin[†] | Macrolide | 50S ribosomal subunit | 733.94 | 2.7 |
| 2 | Azithromycin | Macrolide | 50S ribosomal subunit | 749.00 | 4.0 |
| 3 | Roxithromycin | Macrolide | 50S ribosomal subunit | 837.06 | 3.1 |
| 4 | Clarithromycin | Macrolide | 50S ribosomal subunit | 747.96 | 3.2 |
| 5 | Dirithromycin | Macrolide | 50S ribosomal subunit | 835.09 | 4.2 |
| 6 | Flurithromycin | Macrolide | 50S ribosomal subunit | 751.93 | 2.8 |
| 7 | Josamycin | Macrolide | 50S ribosomal subunit | 828.00 | 2.9 |
| 8 | Midecamycin | Macrolide | 50S ribosomal subunit | 813.98 | 2.6 |
| 9 | Miocamycin | Macrolide | 50S ribosomal subunit | 898.05 | 3.8 |
| 10 | Oleandomycin | Macrolide | 50S ribosomal subunit | 687.87 | 2.6 |
| 11 | Rokitamycin | Macrolide | 50S ribosomal subunit | 828.00 | 3.0 |
| 12 | Spiramycin | Macrolide | 50S ribosomal subunit | 843.07 | 2.1 |
| 13 | Troleandomycin | Macrolide | 50S ribosomal subunit | 813.98 | 4.3 |
| 14 | Tylosin | Macrolide | 50S ribosomal subunit | 916.11 | 1.0 |
| 15 | Telithromycin | Ketolide | 50S ribosomal subunit | 812.02 | 4.2 |
| 16 | Cethromycin | Ketolide | 50S ribosomal subunit | 765.95 | 5.4 |
| 17 | Solithromycin | Ketolide | 50S ribosomal subunit | 845.02 | 4.3 |
| 18 | Quinupristin | Streptogramin | 50S ribosomal subunit | 1022.23 | 4.2 |
| 19 | Dalfopristin | Streptogramin | 50S ribosomal subunit | 690.85 | 2.2 |
| 20 | Rifampicin[†] | Ansamycin | RNA polymerase | 822.95 | 4.0 |
| 21 | Rifabutin | Ansamycin | RNA polymerase | 847.02 | 6.3 |
| 22 | Rifapentine | Ansamycin | RNA polymerase | 877.05 | 5.8 |
| 23 | Rifaximin | Ansamycin | RNA polymerase | 785.89 | 6.9 |
| 24 | Novobiocin[†] | Aminocoumarin | DNA gyrase | 612.63 | 3.3 |
| 25 | Clorobiocin | Aminocoumarin | DNA gyrase | 697.13 | 5.3 |
| 26 | Coumermycin A1 | Aminocoumarin | DNA gyrase | 1110.09 | 4.6 |
| 27 | Vancomycin[†] | Glycopeptide | Cell wall | 1449.27 | −2.6 |
| 28 | Bacitracin | Glycopeptide | Cell wall | 1422.71 | −4.1 |
| 29 | Dalbavancin | Glycopeptide | Cell wall | 1816.71 | 3.8 |
| 30 | Oritavancin | Glycopeptide | Cell wall | 1793.12 | 1.5 |
| 31 | Ramoplanin | Glycopeptide | Cell wall | 2254.09 | −4.8 |
| 32 | Telavancin | Glycopeptide | Cell wall | 1755.65 | −2.1 |
| 33 | Teicoplanin | Glycopeptide | Cell wall | 1879.67 | 0.5 |

*MW and computed logP values were obtained from https://pubchem.ncbi.nlm.nih.gov
[†]Preliminary screens demonstrates the ability of DG-F125 to sensitize *P. aeruginosa* to these antibiotics In another aspect, the present technology provides compositions including a poloxamer covalently attached to a desferrioxamine B-Ga(III) complex, and about 0.1 wt % to about 2.5 wt % of erythromycin, wherein the poloxamer comprises a poly(propylene oxide) block having a molecular weight of about 800 to about 5,000 Daltons and about 10 wt % to about 80 wt % poly(ethylene oxide).

Although not required, in some embodiments the present conjugates may form a micelle. Antibiotics as described herein may be solubilized within the micelle (i.e. loaded into the micelle). For example the present micelles may include one or more antibiotics selected from the group consisting of erythromycin, vancomycin, rifampicin, and novobiocin.

In another aspect, the present technology provides pharmaceutical compositions comprising any of the conjugates described herein, any of the composition described herein, or any of the micelles described herein, and one or more pharmaceutically acceptable excipients.

In another aspect, the present technology provides methods of treating a subject having a bacterial infection comprising administering to the subject an effective amount of any of the compositions described herein or the pharmaceutical compositions described herein. In some embodiments, the bacterial infection is a *Pseudomonas* infection, such as a *P. aeruginosa* infection or an *Acinetobacter* infection, e.g., *A. baumannii*. In other embodiments, the subject is human. The effective amount of the composition may be about 1 mg/kg to about 1000 mg/kg of the subject's body weight. Suitable dosages may include about 1, about 2, about 3, about 4, about 5, about 10, about 20, about 30, about 50, about 100, about 200, about 300, about 400, about 500, about 750, about 1,000 mg/kg of the subject's body weight or a range between and including any two of the foregoing values.

In yet another aspect, the present technology provides methods of inhibiting growth of bacteria including the growth of biofilms comprising exposing the bacteria to an effective amount of any one of the conjugate-containing compositions described herein. While the combination of the present conjugates and antibiotics work best, the conjugates containing, e.g., Ga, are able to inhibit bacterial biofilm growth on their own and therefore contribute to the antibacterial effect of the combination against biofilms. In some embodiments, the bacteria are as described herein. In others the bacteria are *P. aeruginosa* or *A. baumannii*.

In another aspect, the present technology provides kits comprising any of the conjugates described herein, and optionally, any of the antibiotics described herein, and instructions for use. In some embodiments, the kits comprise a 1$^{st}$ package containing the conjugate and a second package containing the antibiotic.

The compositions described herein can be formulated for various routes of administration, for example, by parenteral, rectal, nasal, vaginal administration, or via implanted reservoir. Parenteral or systemic administration includes, but is not limited to, subcutaneous, intravenous, intraperitoneal, and intramuscular injections. The following dosage forms are given by way of example and should not be construed as limiting the instant present technology.

Injectable dosage forms generally include solutions or aqueous suspensions which may be prepared using a suitable dispersant or wetting agent and a suspending agent so long as such agents do not interfere with formation of the micelles described herein. Injectable forms may be prepared with acceptable solvents or vehicles including, but not limited to sterilized water, Ringer's solution, 5% dextrose, or an isotonic aqueous saline solution.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, sex, and diet of the subject, dose intervals, administration routes, excretion rate, and combinations of drug conjugates. Any of the above dosage forms containing effective amounts are well within the bounds of routine experimentation and therefore, well within the scope of the instant present technology. By way of example only, such dosages may be used to administer effective amounts of the antistenotic drugs to the patient and may include about 0.1 mg/kg, about 0.2 mg/kg, about 0.3 mg/kg, about 0.4 mg/kg, about 0.5 mg/kg, about 0.75 mg/kg, about 1 mg/kg, about 1.25 mg/kg, about 1.5 mg/kg, or a range between and including any two of the forgoing values. Such amounts may be administered parenterally as described herein and may take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once per day, per 2 days, per 3 days, per week, per 10 days, per 2 weeks, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4 or more weeks.

The examples herein are provided to illustrate advantages of the present technology and to further assist a person of ordinary skill in the art with preparing or using the micelle compositions of the present technology. To the extent that the compositions include ionizable components, salts such as pharmaceutically acceptable salts of such components may also be used. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Materials:
Pluronic® F127 (F127), poly(ethylene glycol) MW 10,000 ($PEG_{10k}$), poly(ethylene glycol) methyl ether MW 10,000 ($mPEG_{10k}$), sodium hypochlorite solution (NaClO solution), sodium bromide (NaBr), 2,2,6,6-tetramethyl-1-piperidinyloxy free radical (TEMPO), N-ethyl-N'-(3-dimethylaminopropyl)-carbodiimide hydrochloride (EDC), N,N-diisopropylethylamine (DIPEA), gallium(III) nitrate hydrate ($Ga(NO_3)_3.H_2O$), erythromycin (ERY), and novobiocin sodium (NVB), Mueller-Hinton Broth 2 (MHB), and Mueller-Hinton Agar 2 (MHA) were purchased from Sigma-Aldrich (St. Louis, Mo.). 1-Hydroxybenzotriazole hydrate (HOBt) was purchased from Chem-Impex International (Wood Dale, Ill.). Desferrioxamine mesylate (DFO) was purchased from Hospira, Inc. (Lake Forest, Ill.) via the University of Wisconsin Hospital Pharmacy Services. Hydrochloric acid 12N (HCl), dichloromethane (DCM), and diethyl ether were purchased from Fisher Scientific (Fair Lawn, N.J.). Dimethylformamide (DMF) was purchased from Acros Organics (Morris Plains, N.J.). Ethanol (EtOH) was purchased from Decon Labs (King of Prussia, Pa.).

*Pseudomonas aeruginosa* reference strains used were ATCC 27853 and ATCC 15692 (PAO1). MDR *Pseudomonas aeruginosa* strains used (2638, 3072, and 24530) were generously provided by Dr. David Andes at the University of Wisconsin School of Medicine and Public Health. The *Escherichia coli* reference strain used was ATCC 25922. The *Acinetobacter Baumannii* reference strain used was ATCC 19606. The following table shows the drug resistance profiles of the *P. aeruginosa* strains used and additional strains.

TABLE 1

*Pseudomonas aeruginosa* reference strains and multidrug-resistant clinical isolates

| | Strain | Source | Phenotype |
|---|---|---|---|
| 1 | 15692 | ATCC (PAO1) | N/A |
| 2 | 27853 | ATCC | N/A |
| 3 | 3B | Andes collection | N/A |
| 4 | 2638 | Andes collection | DOR-R, IPM-R, MEM-R, FEP-R, CAZ-R, TZP-R, CIP-R, TOB-R |
| 5 | 4304A | Andes collection | N/A |
| 6 | 3068 | Andes collection | DOR-R, IPM-R, MEM-R, FEP-R, CAZ-S, TZP-R, CIP-R |
| 7 | 3070 | Andes collection | DOR-R, IPM-R, MEM-R, FEP-I, CAZ-R, TZP-S, CIP-R |
| 8 | 2757 | Andes collection | N/A |
| 9 | 2627 | Andes collection | N/A |
| 10 | 9139 | Andes collection | DOR-S, IPM-S, MEM-S, FEP-R, CAZ-S, TZP-R, CIP-S, TOB-S |
| 11 | 3072 | Andes collection | DOR-R, IPM-R, MEM-R, FEP-S, CAZ-S, TZP-S, CIP-R, TOB-R |
| 12 | 3071 | Andes collection | DOR-R, IPM-R, MEM-R, FEP-R, CAZ-R, TZP-R, CIP-R |
| 13 | 823 | Andes collection | DOR-S, IPM-S, MEM-S, FEP-R, CAZ-R, TZP-R, CIP-S, TOB-S |
| 14 | 26975 | Andes collection | DOR-S, IPM-S, MEM-S, FEP-R, CAZ-R, TZP-R, CIP-S, TOB-R |
| 15 | 3076 | Andes collection | DOR-R, IPM-R, MEM-R, FEP-I, CAZ-R, TZP-R, CIP-R, TOB-S |
| 16 | 24530 | Andes collection | DOR-R, IPM-R, MEM-R, FEP-R, CAZ-R, TZP-R, CIP-S, TOB-S |

Key:
DOR = doripenem,
IPM = imipenem,
MEM = meropenem,
FEP = cefepime,
CAZ = ceftazidime,
TZP = piperacillin-tazobactam,
CIP = ciprofloxacin,
TOB = tobramycin;
S = susceptible,
I = intermediate,
R = resistant;
N/A = not available Example 1: Synthesis and Characterization of F127-(DFO-Ga)$_2$ (Also Referred to as DG-F125)

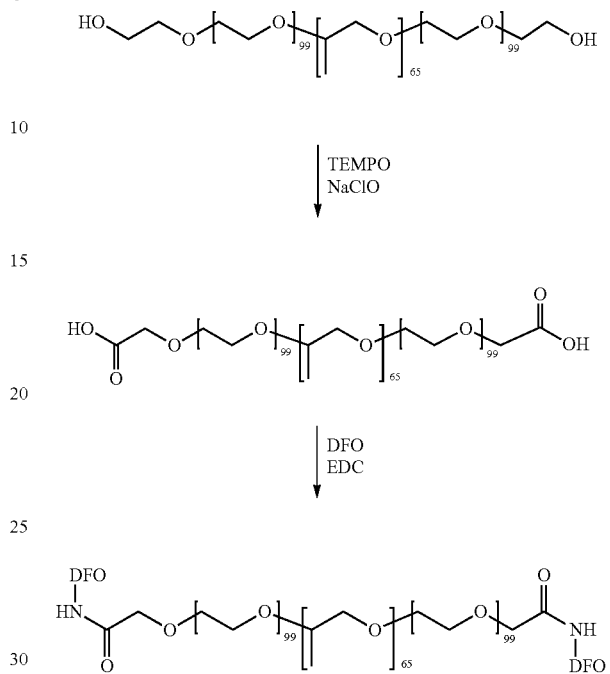

An example of a conjugate according to the present technology was synthesized essentially according to the scheme above. First, the primary alcohols on each end of the poloxamer (F127) were oxidized to carboxylic acids using a procedure similar to that of Araki et al. ("Efficient production of polyrotaxanes from α-cyclodextrin and poly (ethylene glycol)." *Macromolecules* 38, no. 17 (2005): 7524-7527), incorporated by reference herein. The equivalent of 0.6 mmol hydroxyl groups (3.78 g F127, 3 g PEG$_{10k}$, or 6 g mPEG$_{10k}$) was oxidized in water (100 mL) with 100 mg NaBr (0.972 mmol), 100 mg TEMPO (0.640 mmol), and 10 mL NaClO solution (10-15% available chlorine) at pH 10 for 15 minutes (r.t.). The reaction was quenched by the addition of EtOH (10 mL) followed by acidification to pH 1 with HCl. The oxidized polymer was extracted with 3×100 mL of DCM followed by drying by rotary evaporation. The dried polymer was then dissolved in hot EtOH and precipitated at −20° C. Another recrystallization from EtOH was performed to obtain the purified product.

Amide coupling of F127-(COOH)$_2$ to DFO was performed as follows. The equivalent of 0.25 mmol carboxylic acid groups (1.575 g F127-(COOH)$_2$) were reacted with 57.4 mg HOBt (0.375 mmol), 71.9 mg EDC (0.375 mmol), 197 mg DFO (0.3 mmol), and 109 μL DIPEA (0.625 mmol) in 75 mL DMF for 24 hours (r.t.). The reaction mixture was poured into 375 mL EtOH and cooled to −20° C. in order to precipitate the polymer-DFO conjugate. Another recrystallization from EtOH was performed to obtain the purified product.

Since DFO chelates Fe(III) in a 1:1 ratio and the DFO(Fe) complex has a characteristic absorbance peak at 430 nm, a DFO standard curve was generated by mixing DFO solutions of known concentrations with excess aqueous $FeCl_3$ and measuring the A430 by UV-Vis spectroscopy (SpectraMax® Plus, Molecular Devices). Polymer-(DFO) conjugates were dissolved in water at 1 mg/mL with excess $FeCl_3$ and the DFO concentration was calculated based on the standard curve. Based on this procedure, it was calculated that 84.6% to 90% of the F127 end groups were capped with DFO, depending on the batch of conjugate.

F127-$(DFO)_2$ was then complexed with excess gallium as follows. The equivalent of 0.15 mmol DFO (1.25 g F127-$(DFO)_2$) was dissolved in water (50 mL) with 0.165 mmol Ga(III) (69 mg $Ga(NO_3)_3 \times H_2O$, 16.7% Ga) and stirred for one hour (r.t.). The solution was dialyzed against a 7,000 MWCO membrane for 24 hours to remove uncomplexed Ga(III) and lyophilized. The lyophilized product was recrystallized from EtOH to obtain the purified product.

The amount of Ga complexed to each polymer-(DFO) conjugate was quantified by atomic absorption spectroscopy (932 AA, GBC Scientific) using a gallium hollow cathode lamp and metal detection at 294.4 nm. A gallium standard curve was generated by dissolving known amounts of $Ga(NO_3)_3 \cdot xH_2O$ in water. Polymer-(DFO-Ga) conjugates were dissolved in water at 2 mg/mL and the Ga concentration was calculated based on the standard curve. (approximately 105 to 114% of the DFO concentration, depending on the batch, likely due to dialysis incompletely removing unbound ions).

Example 2: Cytotoxicity of F127-$(DFO-Ga)_2$

The cytotoxicity of F127-$(DFO-Ga)_2$ was evaluated against J774.A1 murine macrophage cells in Dulbecco's Modified Eagle Medium (DMEM) supplemented with 10% heat-inactivated fetal bovine serum. Cells were seeded at 3000 cells/well in 96-well plates and cultured at 37° C. for 24 hours before treatment with equivalent concentrations of either free DFO, F127-$(DFO)_2$, or F127-$(DFO-Ga)_2$. Following a 48 hour incubation, cell viability was assessed using a metabolism-based resazurin assay, in which the resazurin substrate was added to each well and incubated for 4 hours before measuring the fluorescent emission intensity at 590 nm (560 nm excitation wavelength).

Preliminary in vivo acute toxicity was determined in a pilot MTD study using six-week old female BALB/c mice. The animals were dosed with the equivalent of approximately 100 mg/kg DFO-Ga by IV injection into the tail vein. For mice receiving multiple doses of F127-$(DFO-Ga)_2$, successive doses were administered every other day (Table 2). Body weight and food consumption was monitored up until day 18 of the study, after which the animals were sacrificed, and their organs were weighed and sectioned for histology.

Figure 7:
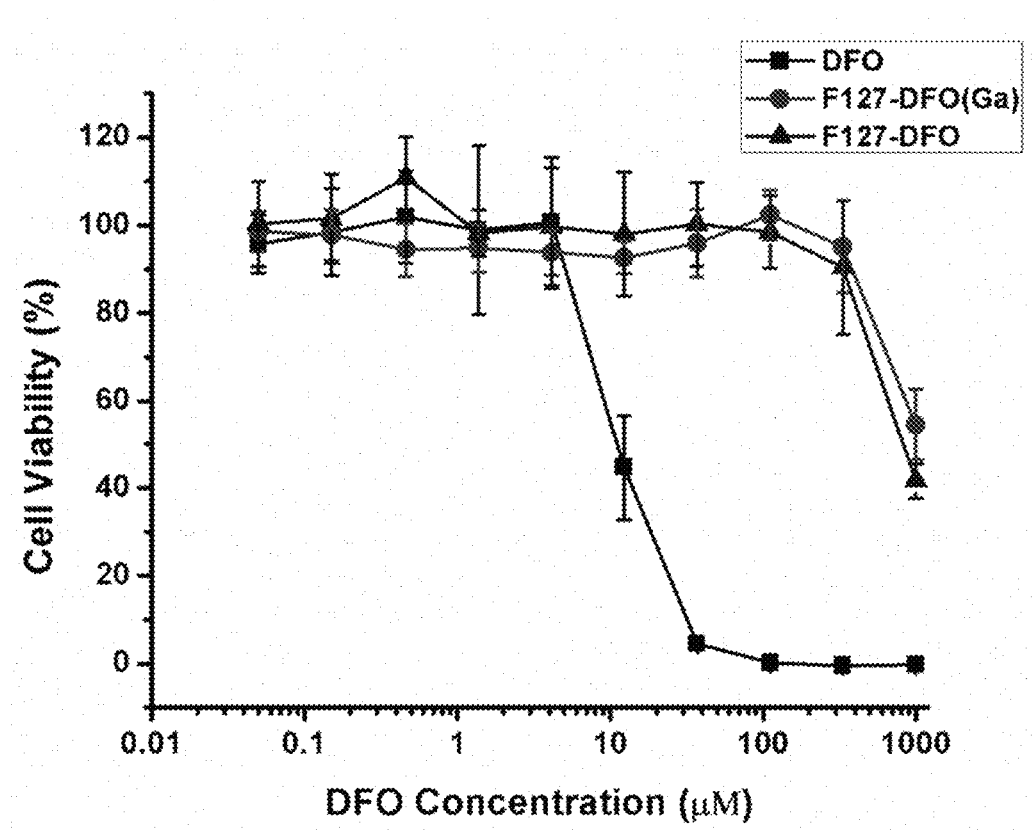
FIG. 7 shows mouse macrophage J774.A1 cytotoxicity study comparing DFO, F127-(DFO)$_2$, and F127-(DFO-Ga)$_2$.
Figure 9C:
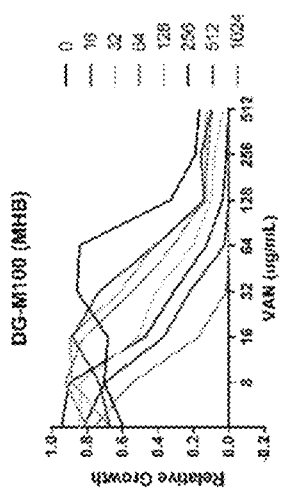
FIGS. 9A-9E shows PAO1 dose response between VAN and varying the concentration of DG-F125, DG-P100, or DG-M100, DG-P40, or DG-M50.
Figure 9E:
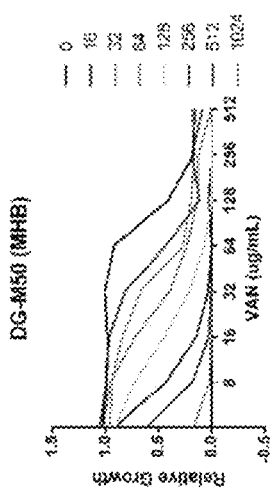
Figure 9B:
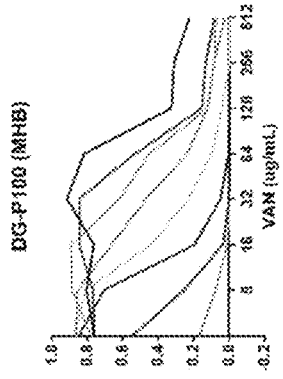
Figure 9D:
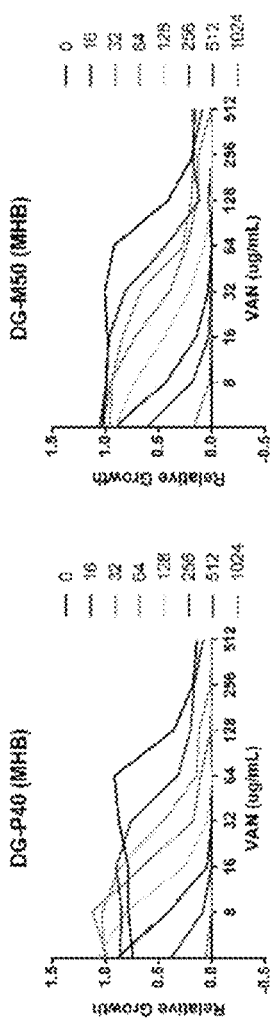
Figure 9A:
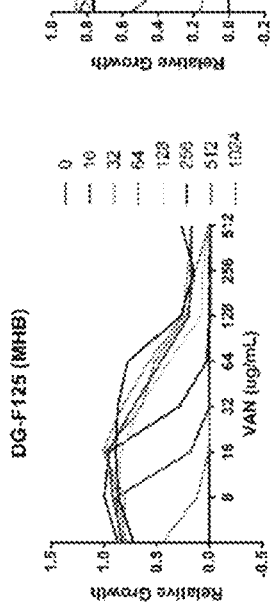
Figure 10A:
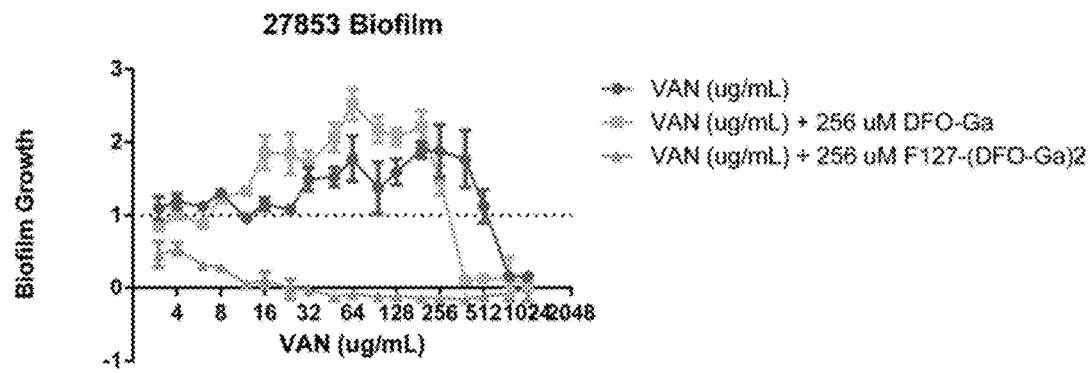
FIGS. 10A-10E show the growth of biofilms for various bacteria in the presence of VAN, VAN+256 uM DFO-Ga, and VAN+256 uM F127-(DFO-Ga)$_2$ for ATCC 27853 (10A), PAO1 (10B), MDR 2638 (10C), MDR 3072 (10D), MDR 24530 (10E).
Figure 10B:
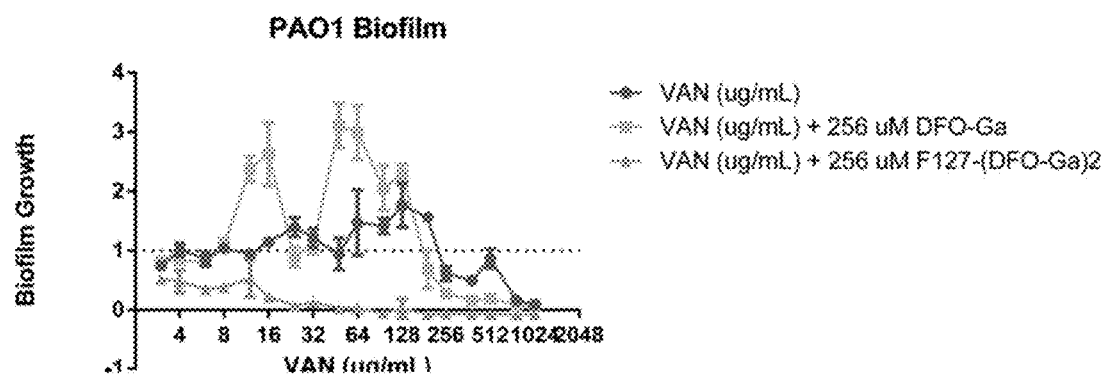
Figure 10C:
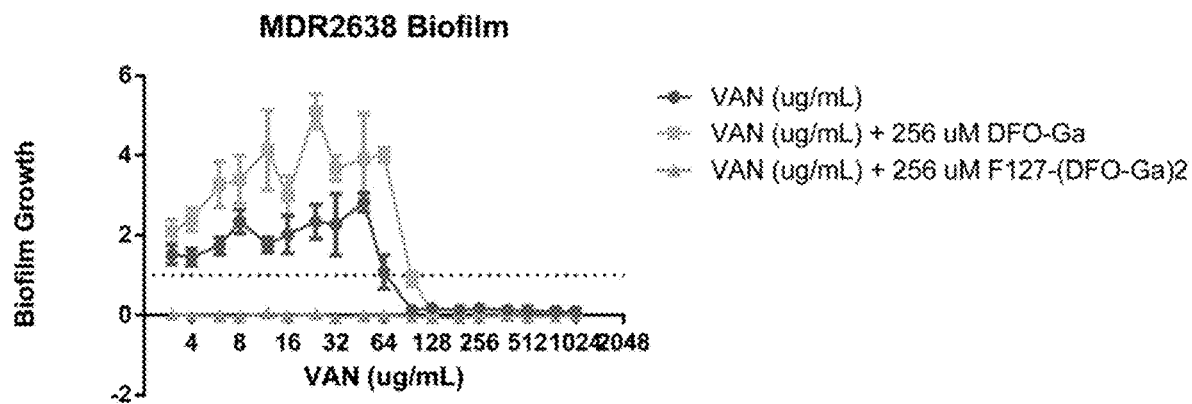
Figure 10D:
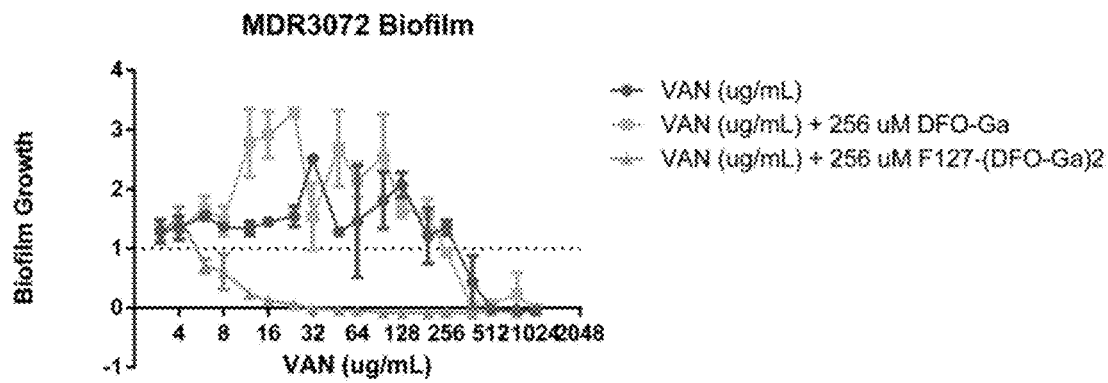
Figure 10E:
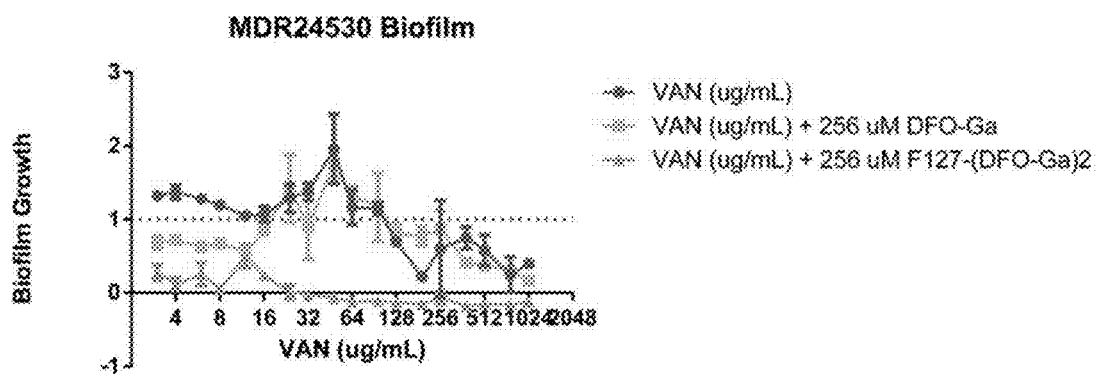

Both F127-$(DFO)_2$ and F127-$(DFO-Ga)_2$ were 100-fold less toxic to the mouse macrophage J774.A1 cell line than free DFO (FIG. 7). F127-$(DFO-Ga)_2$ was well tolerated in vivo as well, with no significant changes in body or organ weight. Tissue samples of organs were also snap-frozen, sectioned and analyzed by a board-certified pathologist; for all doses investigated, no organ damage was observed in any of the mice treated with F127-$(DFO-Ga)_2$.

TABLE 2

| Mouse ID | F127-$(DFO-Ga)_2$ Dose | mg/kg DFO-Ga |
|---|---|---|
| 1 | 4 doses × 24 mg | 4 doses × 117 |
| 2 | 3 doses × 24 mg | 3 doses × 99 |
| 3 | N/A | N/A |
| 4 | 1 dose × 24 mg | 1 dose × 103 |
| 5 | untreated | untreated |

Example 3: Synthesis and Characterization of F127-$(DFO-Ga)_2$/Antibiotic Micelles Erythromycin (ERY) was loaded into F127-$(DFO-Ga)_2$ micelles using the thin film method to form F127-$(DFO-Ga)_2$/ERY micelles, after which the ERY concentration was quantified by measuring the UV absorbance of its acid degradation products at 485 nm using a standard method (Ford, J H, et al. "Colorimetric determination of erythromycin." Anal. Chem. 25, no. 8 (1953): 1195-1197). Typical loading was between 40-60 µg ERY per mg F127-$(DFO-Ga)_2$/ERY (approximately 4-6%). To confirm that F127-$(DFO-Ga)_2$/ERY had formed stable micelles, dynamic light scattering was performed; the F127-$(DFO-Ga)_2$/ERY micelles were approximately 32.9 nm in diameter with a PDI of 0.111, whereas unmodified F127 micelles had a diameter of 24.9 nm (PDI=0.045) as seen in FIG. 1. Similarly, F127-$(DFO-Ga)_2$ micelles could be loaded with novobiocin sodium (NVB), rifampicin (RIF), or vancomycin (VAN).

Example 4: Antibacterial Efficacy of F127-$(DFO-Ga)_2$/Antibiotic Micelles

Antimicrobial efficacy was assessed by the broth microdilution assay in accordance with NCCLS guidelines (Coyle, Marie B. *Manual of antimicrobial susceptibility testing*. American Society for Microbiology, 2005). Organisms were grown overnight on non-selective MHA medium in order to obtain single colonies. Three to five morphologically distinct colonies were touched with a sterile pipet tip and transferred to a culture tube containing MHB (4 mL), and the broth culture was incubated at 37° C. until its turbidity matched a 0.5 McFarland Standard. The inoculum was then diluted 1:20 in sterile water, followed by a 1:10 dilution when inoculating wells of a 96-well plate. Plates were then incubated at 37° C. for 20 hours, and the MIC was read as the lowest concentration of antimicrobial agent that completely inhibited visible growth. For combinations, the fractional inhibitory concentration index (FICI) was calculated using the following equation:

$$FICI = \frac{C_A}{MIC_A} + \frac{C_B}{MIC_B}$$

To determine the dose response of *P. aeruginosa* reference strains (ATCC 27853 and PAO1) to F127-$(DFO-Ga)_2$/ERY, several different ratios of F127-$(DFO-Ga)_2$ and ERY were combined. At a combination of 2 mg/mL (244 µM) F127-$(DFO-Ga)_2$ and 50 µg/mL ERY, neither reference strain exhibited any growth. An equal concentration of F127-$(DFO-Ga)_2$ had no inhibitory effect of bacterial growth, and an equal concentration of ERY resulted in an approximately 40% reduction in the OD600 compared to the positive control. F127-(DFO-Ga)$_2$/ERY was significantly (p<0.001) more effective at inhibiting bacterial growth when the DFO (Ga) complex was conjugated to the F127 polymer, indicating that the free complex was unable to enhance the antibacterial efficacy of ERY.

Figure 3A:
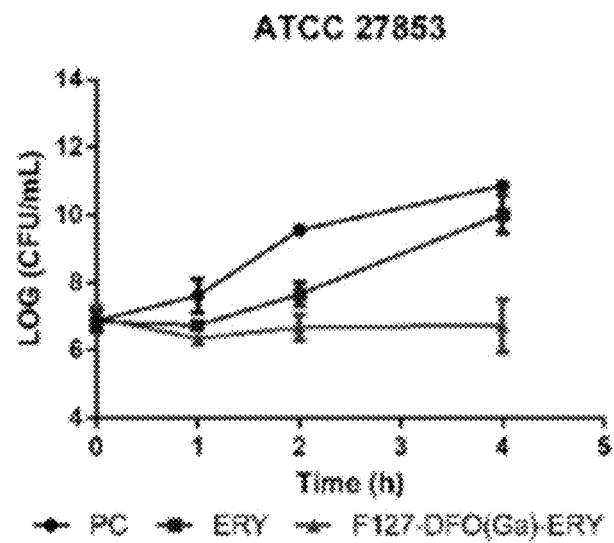
FIGS. 3A and 3B shows the bacteriostatic activity of an illustrative embodiment of the conjugates of the present technology, F127-(DFO-Ga)$_2$/ERY, against two strains of *P. aeruginosa* compared to ERY alone and a positive control (PC).
Figure 3B:
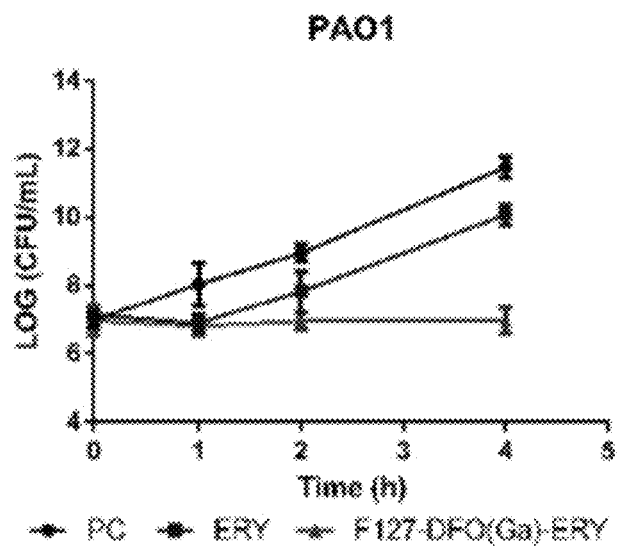
Figure 5:
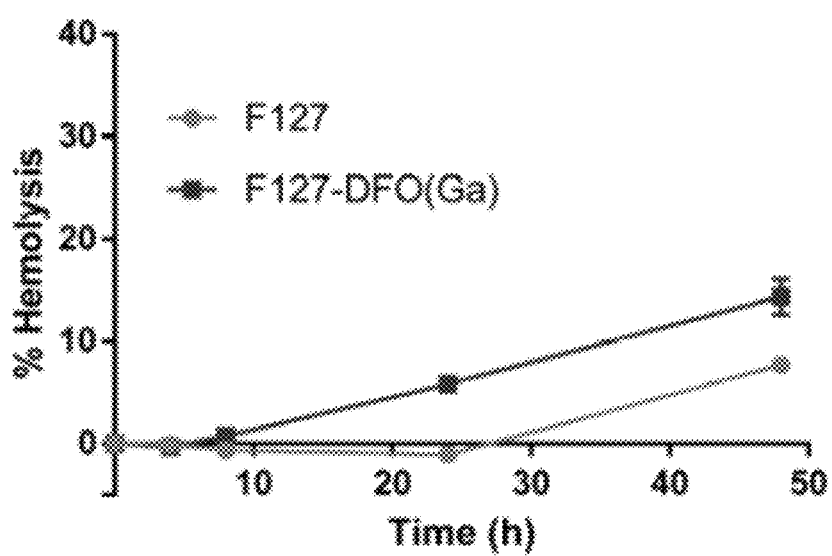
FIG. 5 shows that an illustrative embodiment of the present technology, F127-(DFO-Ga)$_2$ shows little hemolytic activity against bovine RBCs, 14.3% hemolysis (F127-(DFO-Ga)$_2$) vs 7.7% (F127) after 48 hours. (PC=positive control.)
Figure 6A:
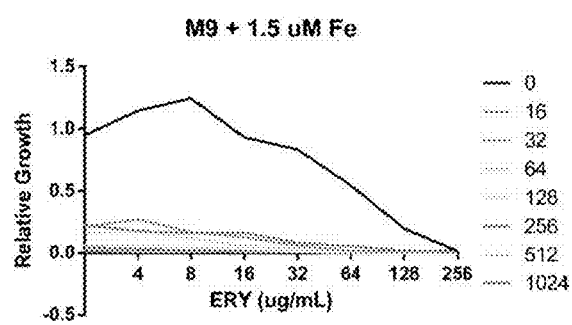
FIGS. 6A-6D shows ATCC 27853 was far more susceptible to F127-(DFO-Ga)$_2$/ERY in M9 media conditions with a small amount of ferric ammonium citrate.
Figure 6B:
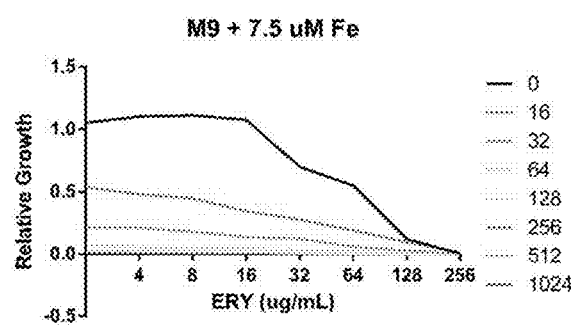
Figure 6C:
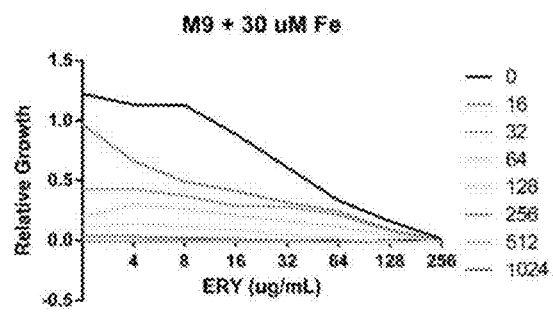
Figure 6D:
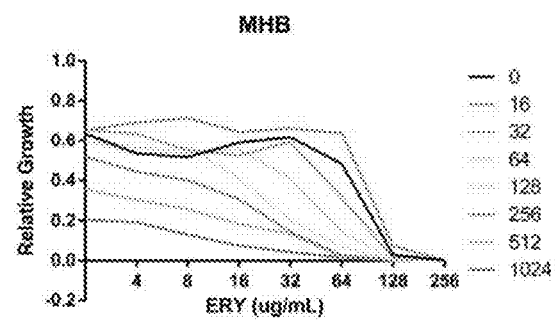

The combination of 244 μM F127-(DFO-Ga)$_2$ and 50 μg/mL ERY was also tested against three clinically isolated MDR strains (2638, 3072, and 24530) of P. aeruginosa obtained from the lab of Dr. David Andes at the University of Wisconsin School of Medicine and Public Health, and was shown to completely inhibit bacterial growth in each case, with F127-(DFO-Ga)$_2$ or ERY alone being similarly ineffective (FIGS. 3A and 3B). In order to determine whether F127-(DFO-Ga)$_2$/ERY exhibits bactericidal activity at this concentration, 4 mL of cation-adjusted Mueller-Hinton broth containing either F127-(DFO-Ga)$_2$/ERY or ERY alone was inoculated. At time points of 0, 1, 2, and 4 hours, a small aliquot was removed from the broth culture, logarithmically diluted in M9 salts, and then spread onto cation-adjusted Mueller-Hinton agar plates. After overnight incubation at 37° C., colonies were counted and the number of CFU/mL was calculated. F127-(DFO-Ga)$_2$/ERY showed bacteriostatic activity against P. aeruginosa strains ATCC 27853 and PAO1, as no change in the number of CFUs was observed over this time course (FIGS. 3A and 3B).

The FICIs for NVB, RIF, or VAN in combination with F127-(DFO-Ga)$_2$ were also determined (Table 3). F127-(DFO-Ga)$_2$ significantly decreased the antibiotic concentrations needed to completely inhibit the growth of each strain of P. aeruginosa. The FICIs for NVB, ERY, and RIF indicate moderate synergy with F127-(DFO-Ga)$_2$ against each strain, while the VAN and F127-(DFO-Ga)$_2$ combination was highly synergistic in activity. Against the reference strain of E. coli, the FICIs were much higher and corresponded to only additive activity, demonstrating that F127-(DFO-Ga)$_2$ specifically targets P. aeruginosa. When DFO-Ga and unmodified F127 were combined with high molecular weight antibiotics (e.g., 600 Da or higher), no significant changes in the antibiotic MICs were observed, indicating that the polymer needs to be conjugated to the DFO-Ga complex in order to enhance antibiotic activity. F127-(DFO-Ga)$_2$ was equally effective against reference and MDR strains of P. aeruginosa, suggesting that its combinations with high molecular weight antibiotics, especially VAN, is a viable strategy for treating carbapenem-resistant infections.

TABLE 3

| | E. coli | | P. aeruginosa | | | |
|---|---|---|---|---|---|---|
| Antibiotic Combination | ATCC 25922 | ATCC 27853 | PAO1 | MDR 2638 | MDR 3072 | MDR 24530 |
| F127-(DFO-Ga)$_2$ | >2048 μM | >2048 μM | >2048 μM | >2048 μM | >2048 μM | >2048 μM |
| NVB | 32 μg/mL | 128 μg/mL | >512 μg/mL | >512 μg/mL | >512 μg/mL | >512 μg/mL |
| NVB + F127-(DFO-Ga)$_2$ | 16 μg/mL 32 μM | 32 μg/mL 128 μM | 256 μg/mL 256 μM | 128 μg/mL 128 μM | 256 μg/mL 256 μM | >256 μg/mL 1024 μM |
| FICI | <0.52 | <0.31 | <0.63 | <0.31 | <0.63 | 1 |
| ERY | 32 μg/mL | 256 μg/mL | 256 μg/mL | 512 μg/mL | 512 μg/mL | 512 μg/mL |
| ERY + F127-(DFO-Ga)$_2$ | 16 μg/mL 512 μM | 64 μg/mL 256 μM | 128 μg/mL 256 μM | 64 μg/mL 256 μM | 128 μg/mL 256 μM | 256 μg/mL 128 μM |
| FICI | <0.75 | <0.38 | <0.63 | <0.25 | <0.38 | <0.56 |
| RIF | 4 μg/mL | 16 μg/mL | 16 μg/mL | 8 μg/mL | 16 μg/mL | 16 μg/mL |
| RIF + F127-(DFO-Ga)$_2$ | 2 μg/mL 1024 μM | 8 μg/mL 128 μM | 8 μg/mL 128 μM | 4 μg/mL 64 μM | 8 μg/mL 128 μM | 8 μg/mL 64 μM |
| FICI | <1 | <0.56 | <0.56 | <0.53 | <0.56 | <0.53 |
| VAN | 128 μg/mL | >1024 μg/mL | >1024 μg/mL | 512 μg/mL | >1024 μg/mL | 1024 μg/mL |
| VAN + F127-(DFO-Ga)$_2$ | 64 μg/mL 1024 μM | 32 μg/mL 256 μM | 64 μg/mL 256 μM | 64 μg/mL 128 μM | 64 μg/mL 256 μM | 128 μg/mL 256 μM |
| FICI | <1 | <0.16 | <0.19 | <0.19 | <0.19 | <0.25 |

Example 5: Antibacterial Efficacy of F127-(DFO-Ga)$_2$ and Antibiotic by Disk Diffusion The combination of F127-(DFO-Ga)$_2$ and specified amounts of ERY, NVB, RIF, and VAN were tested against P. aeruginosa (reference strains ATCC 27853/PAO1 and MDR strains 3072/24530). To study the effects, MHA plates with and without 256 μM F127-(DFO-Ga)$_2$ were prepared. Single colonies were grown in MHB to match a 0.5 McFarland standard. A sterile cotton swab was dipped into the various MDR strain inoculums and spread evenly over the surface of the agar plates. Purchased antibiotic-containing disks at fixed concentrations (Table 4) were placed on the surface of each plate and incubated overnight at 37° C. Zones of inhibition were measured the following morning. Measurements included the diameter (d) of the antibiotic disk (6 mm) and are reported in terms of diameters and areas. For example, a measurement of "0" means there was no zone of inhibition as the bacteria was able to grow underneath the disk. Values in parentheses are regions where some growth is still visible, though notably less than the control growth regions. Typically for diameters, R<10, I 11-15, and S>15 where R=resistance, I=intermediate resistance, and S=susceptible. Several of the combinations of ERY, NVB, RIF, or VAN with F127-(DFO-Ga)$_2$ provided increased bacteriostatic activity. It is speculated that the antibiotic activity increase achieved by the combination may be due to F127-(DFO-Ga)$_2$ targeting the outer membrane of the bacteria specifically, meaning that its combination with high molecular weight antibiotics can be a clinically relevant treatment option for MDR P. aeruginosa infections.

TABLE 4

| | NVB (30 μg) | | ERY (15 μg) | | RIF (5 μg) | | VAN (30 μg) | |
|---|---|---|---|---|---|---|---|---|
| | d·mm | A·mm² | d·mm | A·mm² | d·mm | A·mm² | d·mm | A·mm² |
| 27853 | 7.5 | 44 | 11 | 95 | 0 | 0 | 0 | 0 |
| +DG-F125 | 10 | 79 | 12 (29) | 113 (660) | 10 (19) | 79 (283) | 16 | 201 |
| PAO1 | 0 | 0 | 9 | 64 | 6.5 | 33 | 0 (9) | 0 (64) |
| +DG-F125 | 10 | 79 | 11 | 95 | 12 | 113 | 17 | 227 |
| 3072 | 0 | 0 | 0 (19) | 0 (283) | 0 | 0 | 0 | 0 |
| +DG-F125 | 0 | 0 | 19 | 283 | 14 | 154 | 16 | 201 |
| 24530 | 0 | 0 | 0 (13) | 0 (133) | 0 | 0 | 0 | 0 |
| +DG-F125 | 0 | 0 | 9 (20) | 64 (314) | 0 (13) | 0 (133) | 7 (12) | 38 (113) |

Example 6: TEM Study of *P. aeruginosa* with F127-(DFO-Ga)₂/ERY

A liquid culture of *P. aeruginosa* ATCC 27853 was grown in MHB at 37° C. until the turbidity matched a 1.0 McFarland Standard. The liquid culture was then divided into three aliquots (1 mL) and centrifuged at 10,000 RPM for 5 minutes to pellet the bacterial cells and the supernatant was removed. The pellets were then resuspended in either MHB, MHB containing 650 uM (DFO-Ga), or MHB containing 650 uM F127-(DFO-Ga)₂ and incubated at 37° C. for two hours. The cultures were then centrifuged at 10,000 RPM for 5 minutes and washed with 10 mM Na-EDTA three times to remove surface-adsorbed metals, and were then resuspended in PBS.

Fixation.

Samples were immersion fixed for 2 hours in 2.5% glutaraldehyde, 2.0% paraformaldehyde buffered in 0.1M sodium phosphate buffer (PB) at room temperature (RT). The primary fixed samples were rinsed 5×5 minutes in PB, and post-fixed in 1% osmium tetroxide in 0.1M PB for 1 hour at RT, and rinsed in PB as before.

Dehydration.

The post-fixed and rinsed samples were dehydrated in a graded series of ethanol (EtOH) in the increasing percentages 35, 50, 70, 80, 90%, 95% for 10 minutes and 100% EtOH for 3×10 minutes at RT.

Infiltration and Embedding.

Fully dehydrated samples were infiltrated in increasing concentrations of PolyBed 812 (Polysciences Inc. Warrington, Pa.) and Propylene Oxide (PPO) mixtures in the order shown in Table 5. Embedding and polymerization took place in fresh PolyBed 812 for 48 hours at 60° C.

TABLE 5

| PolyBed 812 | PPO | Time | Temp. |
|---|---|---|---|
| 25% | 75% | 60 min. | RT |
| 50% | 50% | 60 min. | RT |
| 75% | 25% | Overnight | RT |
| 100% | 0% | 4 × 45 min. | 60° C. |

Sectioning and Documenting.

The samples were sectioned on a Leica EM UC6 ultramicrotome at 90 nm. The sections were collected on Cu, 300 mesh thin-bar grids (EMS Hatfield, Pa.), and post-stained in uranyl acetate and lead citrate. The sectioned samples were viewed at 80 kV on a Philips CM120 transmission electron microscope, equipped with MegaView III camera (Olympus Soft Imaging System Lakewood, Colo.).

Example 7: Inhibition of *P. aeruginosa* Biofilm Formation by F127-(DFO-Ga)₂/Antibiotic For static biofilms, the methods of Hentzer et al. ("Alginate overproduction affects *Pseudomonas aeruginosa* biofilm structure and function." Journal of bacteriology 183, no. 18 (2001): 5395-5401) and O'Toole et al. ("Investigation of the Alamar Blue (resazurin) fluorescent dye for the assessment of mammalian cell cytotoxicity." *European Journal of Biochemistry* 267, no. 17 (2000): 5421-5426) are used. Briefly, a 100 μL of a 0.5 McFarland Standard culture of *P. aeruginosa* (reference strains ATCC 27853/PAO1 and MDR strains 2638/3072/24530) is added to 96-well microtiter plates and grown overnight at 37° C. Biofilm formation is detected by staining with 1% crystal violet, washing with water, and solubilization of cell-associated dye with ethanol, after which the dye is quantified by measuring the A595 of each well. The biofilm mass in wells treated with F127-(DFO-Ga)₂/ERY will be less than those treated with equivalent concentrations of F127, F127-(DFO-Ga)₂, ERY, DFO (Ga) or DFO(Ga)+ERY.

Confocal laser scanning microscopy (CSLM) is used to visualize biofilm formation of *P. aeruginosa*. CLSM images of biofilms were taken following biofilm growth under static conditions in LabTek Chambered Slides Each slide chamber was inoculated as previously described, and slides were incubated for 1 hour at 37° C. to allow for cell adhesion. Chambers were then washed to remove unadhered bacteria, and MHB containing a sub-inhibitory concentration of VAN and F127-(DFO-Ga)$_2$ was added to each chamber. Slides were incubated for 24 hours at 37° C., after which planktonic cells were washed away and the remaining biofilm-associated cells were stained with the green fluorescent dye SYTO13. Stained biofilms were directly imaged with a Zeiss LSM 710 Confocal Microscope.

Figure 11A:
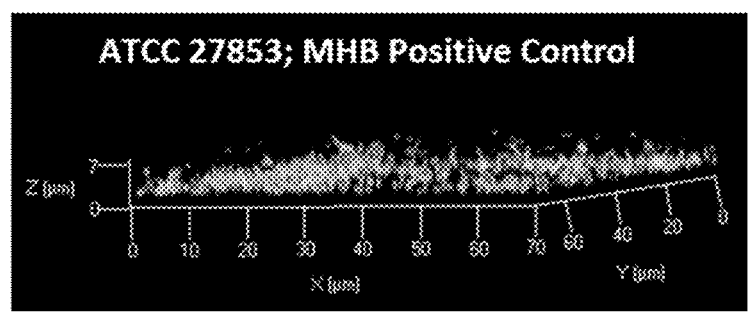
FIGS. 11A-11D show CLSM biofilm images.
Figure 11B:
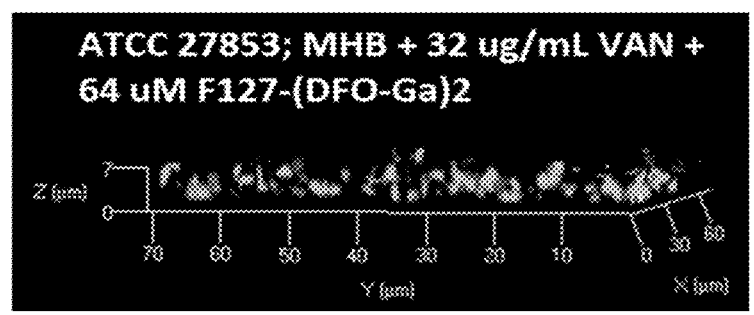
Figure 11C:
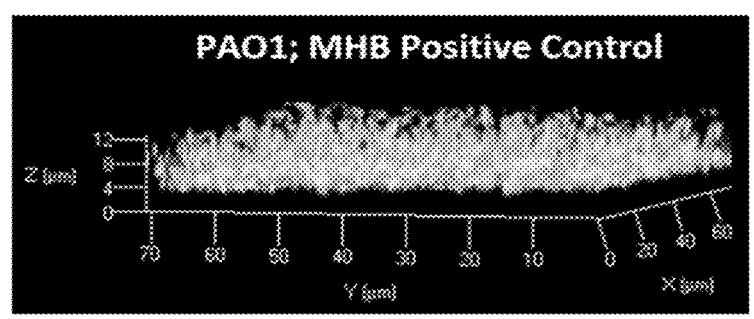
Figure 11D:
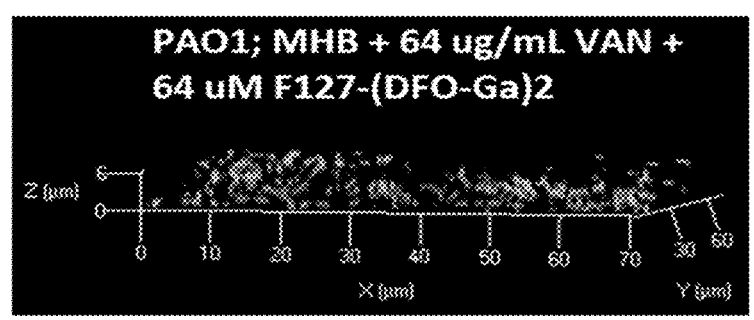

The biofilms formed by each strain of *P. aeruginosa* in the presence of F127-(DFO-Ga)$_2$ in combination with VAN were studied. F127-(DFO-Ga)$_2$ significantly reduced the amount of biofilms formed by each strain of *P. aeruginosa* under static conditions and was able to completely prevent any biofilm formation at sub-inhibitory antibiotic concentrations. Representative plots of biofilm growth versus VAN concentration with and without 256 uM F127-(DFO-Ga)$_2$ are shown in FIGS. 10A-E. Sub-inhibitory concentrations of VAN and F127-(DFO-Ga)$_2$ prevented *P. aeruginosa* reference strain biofilms from proliferating when imaged by CLSM. For strain ATCC 27853, biofilm density decreased with biofilm thickness remaining relatively unchanged (FIGS. 11A, 11B). For strain PAO1, biofilm density and thickness both significantly decreased (See FIGS. 11C, 11D).

In the setting of real world infections, pathogenic bacteria need to compete with the host for resources, and since MHB is a very nutrient-rich media, several studies were performed to see how well F127-(DFO-Ga)$_2$ acts on *P. aeruginosa* under minimal growth conditions. To simulate a nutrient-poor environment, M9 media supplemented with a small amount of ferric ammonium citrate was used. Under nutrient-poor conditions, strain ATCC 27853 was far more susceptible to F127-(DFO-Ga)$_2$ than it was in MHB, suggesting that the construct may be even more effective in a real world scenario than under the ideal in vitro conditions represented by MHB (FIG. 6A-6D).

Example 8: Synthesis and Characterization of Various Polymer Conjugates

To investigate the effects of different polymer characteristics, additional conjugates were prepared: DG-P100 (PEG10k-(DFO-Ga)$_2$), DGM100 (mPEG10k-DFO-Ga), DG-P40 (PEG 4k-(DFO-Ga)$_2$), and DG-M50 (PEG 5k-(DFO-Ga)$_2$) were synthesized and characterized. Amide coupling of mPEG$_{10k}$-COOH ($M_n$=8,710 g/mol, PDI=1.1) or PEG$_{10k}$-(COOH)$_2$ ($M_n$=9,948 g/mol, PDI=1.14) to DFO was performed as follows. The equivalent of 0.25 mmol carboxylic acid groups (2.5 g mPEG$_{10k}$-COOH or 1.25 g PEG$_{10k}$-(COOH)$_2$) were reacted with 57.4 mg HOBt (0.375 mmol), 71.9 mg EDC (0.375 mmol), 197 mg DFO (0.3 mmol), and 109 µL DIPEA (0.625 mmol) in 75 mL DMF for 24 hours (r.t.). The reaction mixture was poured into 375 mL EtOH and cooled to −20° C. in order to precipitate the polymer-DFO conjugate. Another recrystallization from EtOH was performed to obtain the purified product. The complexation of the PEG polymers to Ga and purification steps were performed as reported above. Similarly, DG-P40 and DG-M50 were synthesized using PEG$_{4k}$-(COOH)$_2$ and PEG$_{5k}$-(COOH)$_2$, respectively. Table 6 shows physical data for three of the foregoing conjugates.

TABLE 6

| Polymer | Polymer Abbreviation | DFO (µM) @ 1 mg/mL | % Conversion to DFO | Ga (µM) @ 1 mg/mL | Ga: DFO |
|---|---|---|---|---|---|
| mPEG$_{10k}$-(DFO-Ga) | DG-M100 | 101 ± 10 | 107 ± 10 | 93 ± 8 | 0.92 |
| PEG$_{10k}$-(DFO-Ga)$_2$ | DG-P100 | 114 ± 3 | 63.4 ± 1.8 | 108 ± 7 | 0.95 |
| F127-(DFO-Ga)$_2$ | DG-F125 | 156 ± 4 | 107 ± 3 | 140 ± 10 | 0.90 |

Example 9: Anti-Bacterial Efficacy of Various Polymer Conjugates

The antibacterial efficacy of the various polymer conjugates were determined as described in Example 4. Against both ATCC 27853 (FIGS. 8A-8E) and PAO1 (FIGS. 9A-9E), all of the conjugates significantly enhanced the activity of VAN, with the dumbbell structured conjugates F127-(DFO-Ga)$_2$ (also referred to as DG-F125), DG-P100, and DG-P40 performing approximately two-fold better than their lollipop structured counterparts of similar size. Results are shown in Tables 7-9.

TABLE 7

| Polymer | Polymer Abbreviation | *E. coli* ATCC 25922 | *P. aeruginosa* ATCC 27853 | *P. aeruginosa* PAO1 |
|---|---|---|---|---|
| mPEG$_{10k}$-(DFO-Ga) | DG-M100 | >896 µM | 448 µM | 448 µM |
| PEG$_{10k}$-(DFO-Ga)$_2$ | DG-P100 | >896 µM | 448 µM | 448 µM |
| F127-(DFO-Ga)$_2$ | DG-F125 | >896 µM | 448 µM | 448 µM |
| DFO-Ga | DG | 1792 µM | 896 µM | 896 µM |
| ERY | N/A | 32 µg/mL | >128 µg/mL | >128 µg/mL |
| NVB | N/A | 48 µg/mL | >128 µg/mL | >128 µg/mL |

TABLE 8

| Polymer | Abbreviation | E. coli ATCC 25922 | P. aeruginosa ATCC 27853 | P. aeruginosa PAO1 |
|---|---|---|---|---|
| mPEG$_{10k}$-(DFO-Ga) + ERY | DG-M100 + ERY | 112 µM + 32 µg/mL* | 112 µM + 24 µg/mL** | 112 µM + 32 µg/mL** |
| mPEG$_{10k}$-(DFO-Ga) + NVB | DG-M100 + NVB | 112 µM + 32 µg/mL | 224 µM + 48 µg/mL** | 112 µM + 24 µg/mL** |
| PEG$_{10k}$-(DFO-Ga)$_2$ + ERY | DG-P100 + ERY | 112 µM + 32 µg/mL* | 112 µM + 24 µg/mL** | 112 µM + 24 µg/mL** |
| PEG$_{10k}$-(DFO-Ga)$_2$ + NVB | DG-P100 + NVB | 112 µM + 32 µg/mL | 224 µM + 48 µg/mL** | 112 µM + 24 µg/mL** |
| F127-(DFO-Ga)$_2$ + ERY | DG-F127 + ERY | 112 µM + 32 µg/mL* | 224 µM + 32 µg/mL** | 112 µM + 32 µg/mL** |
| F127-(DFO-Ga)$_2$ + NVB | DG-F127 + NVB | 112 µM + 32 µg/mL | 224 µM + 64 µg/mL | 112 µM + 64 µg/mL |
| DFO-Ga + ERY | DG + ERY | 112 µM + 32 µg/mL* | 224 µM + >96 µg/mL*** | 224 µM + 96 µg/mL |
| DFO-Ga + NVB | DG + NVB | 112 µM + 32 µg/mL | 224 µM + 64 µg/mL | 224 µM + >96 µg/mL*** |

*= No reduction in antibiotic concentration
** 32 More than two fold reduction in antibiotic concentration
***= Growth detected at highest concentrations tested

TABLE 9

| Polymer | Abbreviation | E. coli ATCC 25922 | P. aeruginosa ATCC 27853 | P. aeruginosa PAO1 |
|---|---|---|---|---|
| mPEG$_{10k}$-(DFO-Ga) + ERY | DG-M100 + ERY | 1.13* | <0.44** | <0.5** |
| mPEG$_{10k}$-(DFO-Ga) + NVB | DG-M100 + NVB | 0.92 | <0.88** | <0.44** |
| PEG$_{10k}$-(DFO-Ga)$_2$ + ERY | DG-P100 + ERY | 1.13* | <0.44** | <0.44** |
| PEG$_{10k}$-(DFO-Ga)$_2$ + NVB | DG = P100 + NVB | 0.92 | <0.88** | <0.44** |
| F127-(DFO-Ga)$_2$ + ERY | DG-F127 + ERY | 1.13* | <0.75** | <0.5** |
| F127-(DFO-Ga)$_2$ + NVB | DG-F127 + NVB | 0.92 | <1.0 | <0.75 |
| DFO-Ga + ERY | DG + ERY | 1.06* | 1.0*** | <1.0 |
| DFO-Ga + NVB | DG + NVB | 0.73 | <0.75 | 1.0*** |

*= No reduction in antibiotic concentration
**= More than two fold reduction in antibiotic concentration
***= Growth detected at highest concentrations tested Example 10: Anti-Bacterial Efficacy of DG-F125 and DG-M50 Against *Acinetobacter baumannii* (ATCC 19606)

Figure 12A:
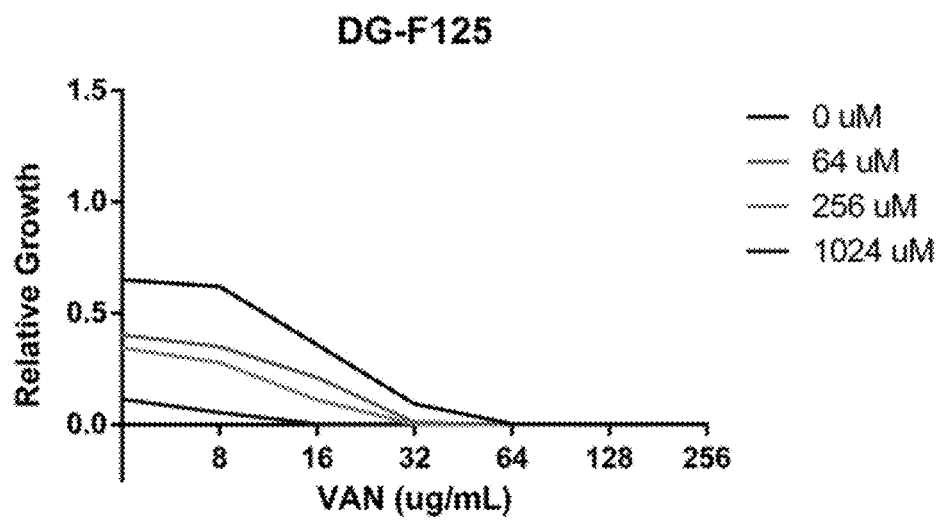
FIGS. 12A and 12B show dose response between VAN and varying concentrations of DG-F125 (12A) and DG-M50 (12B) against *Acinetobacter baumannii* (ATCC 19606).
Figure 12B:
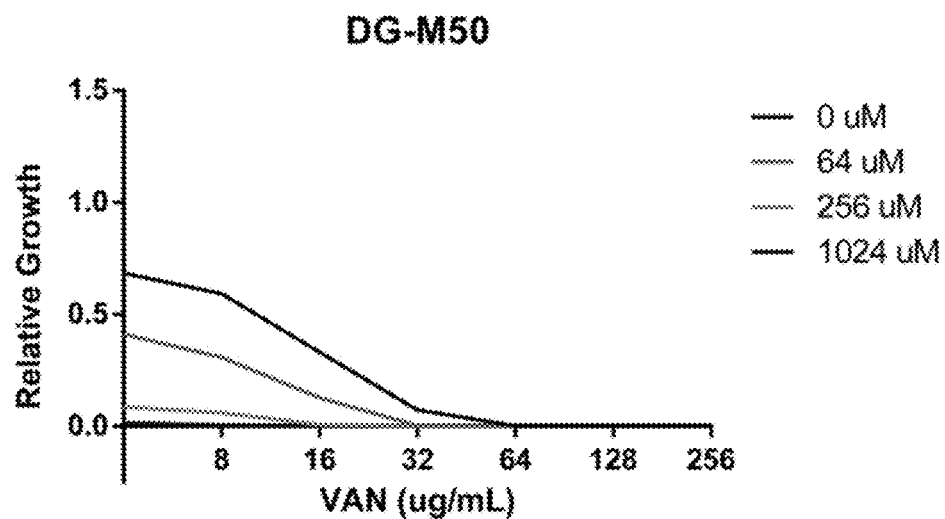

The antibacterial efficacy of the DG-F125 and DG-M50 against *Acinetobacter baumannii* (ATCC19606) was determined essentially as described in Example 4, but using *A. baumannii* rather than *P. aeruginosa*. Results are shown in FIGS. 12A (DG-F125) and 12B (DG-M50). Both conjugates significantly enhanced the activity of VAN.

EQUIVALENTS

While certain embodiments have been illustrated and described, a person with ordinary skill in the art, after reading the foregoing specification, can effect changes, substitutions of equivalents and other types of alterations to the conjugates and micelles of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A micelle comprising:
    a conjugate comprising a water-soluble polymer covalently attached to at least one siderophore-metal ion complex wherein the water-soluble polymer is selected from polyethylene glycol (PEG) or a poloxamer, the siderophore is desferrioxamine B, and the metal is selected from Fe, Ga, Zn, Co, or Al and
    an antibiotic solubilized within the micelle.

2. The micelle of claim 1 wherein the water soluble polymer is a poloxamer comprising a poly(propylene oxide) block having a weight average molecular weight of about 800 to 5,000 Daltons (Da).

3. The micelle of claim 2 wherein the poloxamer comprises a poly(propylene oxide) block having a weight average molecular weight of about 2,500 to about 4,500 Da.

4. The micelle of claim 1 wherein the poloxamer comprises about 10 wt % to about 80 wt % poly(ethylene oxide).

5. The micelle of claim 4 wherein the poloxamer comprises about 60 wt % to about 80 wt % poly(ethylene oxide).

6. The micelle of claim 1 wherein the water-soluble polymer is PEG having a weight average molecular weight of about 200 to about 20,000 Da.

7. The micelle of claim 6 wherein the PEG has a weight average molecular weight of about 1,000 to about 12,500 Da.

8. The micelle of claim 1 wherein the siderophore is covalently attached to the water-soluble polymer through an amide bond.

9. The micelle of claim 1 wherein the metal ion is Ga(III).

10. The micelle of claim 1 wherein the amount of antibiotic in the micelle is about 0.05 wt % to about 10 wt %.

11. The micelle of claim 1 wherein the antibiotic has a molecular weight greater than about 600 Da.

12. The micelle of claim 1 wherein the antibiotic is one or more selected from the group consisting of macrolides, ketolides, streptogramin, ansamycin, aminocoumarin, and glycopeptide.

13. The micelle of claim 1 wherein the antibiotic has a molecular weight less than about 600 Da.

14. The micelle of claim 1 wherein the antibiotic is one or more selected from the group consisting of aminoglycosides, carbapenems, cephalosporins, monobactams, penicillins, fluoroquinolones, and rifampicin.

15. The micelle of claim 1 wherein the antibiotic is one or more selected from the group consisting of erythromycin, novobiocin, gentamycin, tobramycin, doripenem, imipenem, meropenem, cefoperazone, ceftazidime, cefepime, ceftobiprole, aztreonam, carbenicillin, piperacillin/tazobactam, colistin, ciprofloxacin, levofloxacin, rifampicin, and vancomycin.

16. The micelle of claim 1 wherein the antibiotic is one or more selected from the group consisting of vancomycin, erythromycin, novobiocin, and rifampicin.

17. The micelle of claim 1, wherein the poloxamer is covalently attached to the siderophore, the metal ion is Ga(III); the poloxamer comprises a poly(propylene oxide) block having a weight average molecular weight of 800 to 5,000 Da and about 10 wt % to about 80 wt % poly(ethylene oxide); and the micelle comprises about 0.05 wt % to about 10 wt % of an antibiotic solubilized within the micelle selected from the group consisting of vancomycin, rifampicin, erythromycin, and novobiocin.

18. A pharmaceutical composition comprising the micelle of claim 1 and one or more pharmaceutically acceptable excipients.

19. The composition of claim 18 wherein the micelle comprises about 0.05 wt % to about 10 wt % of the antibiotic solubilized within the micelle.

* * * * *